US00PP34128P2

(12) United States Plant Patent
Lubbe

(10) Patent No.: US PP34,128 P2
(45) Date of Patent: Apr. 12, 2022

(54) ***GERANIUM* PLANT NAMED 'KELLY ANNE'**

(50) Latin Name: *Geranium wallichianum*
Varietal Denomination: KELLY ANNE

(71) Applicant: Molter B.V., Noordwijkerhout (NL)

(72) Inventor: Remy Lubbe, Noordwijkerhout (NL)

(73) Assignee: Molter B.V.

( * ) Notice: Subject to any disclaimer, the term of this patent is extended or adjusted under 35 U.S.C. 154(b) by 0 days.

(21) Appl. No.: 17/307,413

(22) Filed: May 4, 2021

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./324
CPC ... A01H 5/02; A01H 5/00; A01H 6/42; A01H 6/425
See application file for complete search history.

*Primary Examiner* — June Hwu
(74) *Attorney, Agent, or Firm* — Cassandra Bright

(57) ABSTRACT

A new and distinct *Geranium* cultivar named 'KELLY ANNE' is disclosed, characterized by bright pink flowers with darker pink veins. Plants are floriferous and have a neat, mounding and compact growth habit. The flowering period of the new variety is exceptionally long, from approximately May until October and plants are Winter cold hardy to −20 degrees Celsius. The new variety is a *Geranium*, typically produced as an outdoor ornamental plant.

3 Drawing Sheets

Latin name of the genus and species: *Geranium wallichianum.*

Variety denomination: 'KELLY ANNE'.

BACKGROUND OF THE INVENTION

The new cultivar is a product of chance discovery. The new variety originated as a result of a planned breeding program conducted in Noordwijkerhout, the Netherlands. The new variety is the result of a crossing of two different unnamed, unpatented *Geranium wallichianum* plants. The crossing resulting in the new variety was made during 2017.

The new variety was selected by the inventor, Remy Lubbe during the Summer of 2018 at a research greenhouse in Noordwijkerhout, the Netherlands. After identifying the new variety as a potentially interesting selection, the inventor continued confidential trial growing of 'KELLY ANNE' to assess the stability of characteristics unique to this variety.

Asexual reproduction of the new cultivar 'KELLY ANNE' was first performed during Autumn of 2018 at a commercial laboratory in Noordwijkerhout, the Netherlands by meristem tissue culture. Through subsequent propagation by vegetative cuttings, multiple additional generations have been reproduced, having shown that the unique features of this cultivar are stable and reproduced true to type.

SUMMARY OF THE INVENTION

The cultivar 'KELLY ANNE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KELLY ANNE'. These characteristics in combination distinguish 'KELLY ANNE' as a new and distinct *Geranium* cultivar:

1. Bright pink flowers with darker pink veins.
2. Long flowering period from approximately May until October.
3. Neat, mounding and compact growth habit.

4. Very floriferous.
5. Winter hardy to approximately −20 degrees Celsius.

PARENT COMPARISON

Plants of the new cultivar 'KELLY ANNE' are similar to the unnamed seed parent, in most horticultural characteristics. The new variety, however, produces flowers which are more pink in color and produce plants which are more compact. Characteristics of the pollen parent are not available for comparison.

COMMERCIAL COMPARISON

'KELLY ANNE' can be compared to compared to the commercial variety *Geranium* 'Rozanne' U.S. Plant Pat. No. 12,175. Plants of 'Rozanne' are similar to plants of 'KELLY ANNE' in most horticultural characteristics, however, plants of 'Rozanne' produce flower petals colored near Violet-Blue 90A and 90D, whereas the new variety produces petals colored Violet N80C with a base of White N155D. Plants of the new variety are wider than plants of 'Rozanne'.

'KELLY ANNE' can be compared to compared to the commercial variety *Geranium* 'Sylvia's Surprise' U.S. Plant Pat. No. 21,333. Plants of 'Sylvia's Surprise' are similar to plants of 'KELLY ANNE' in most horticultural characteristics, however, plants of however, plants of 'Sylvia's Surprise' produce flower petals colored near Red-Purple 68C flushed Violet-Blue 91C with venation close to Red-Purple 70B, whereas the new variety produces petals colored Violet N80C with a base of White N155D. Plants of the new variety are not as wide as plants of 'Sylvia's Surprise'.

BRIEF DESCRIPTION OF THE PHOTOGRAPHS

The accompanying photograph in FIG. 1 illustrates in full color a typical plant of 'KELLY ANNE' grown outdoors in Noordwijkerhout, the Netherlands. This plant is approximately 12 months old, shown planted in the ground.

Figure 1:
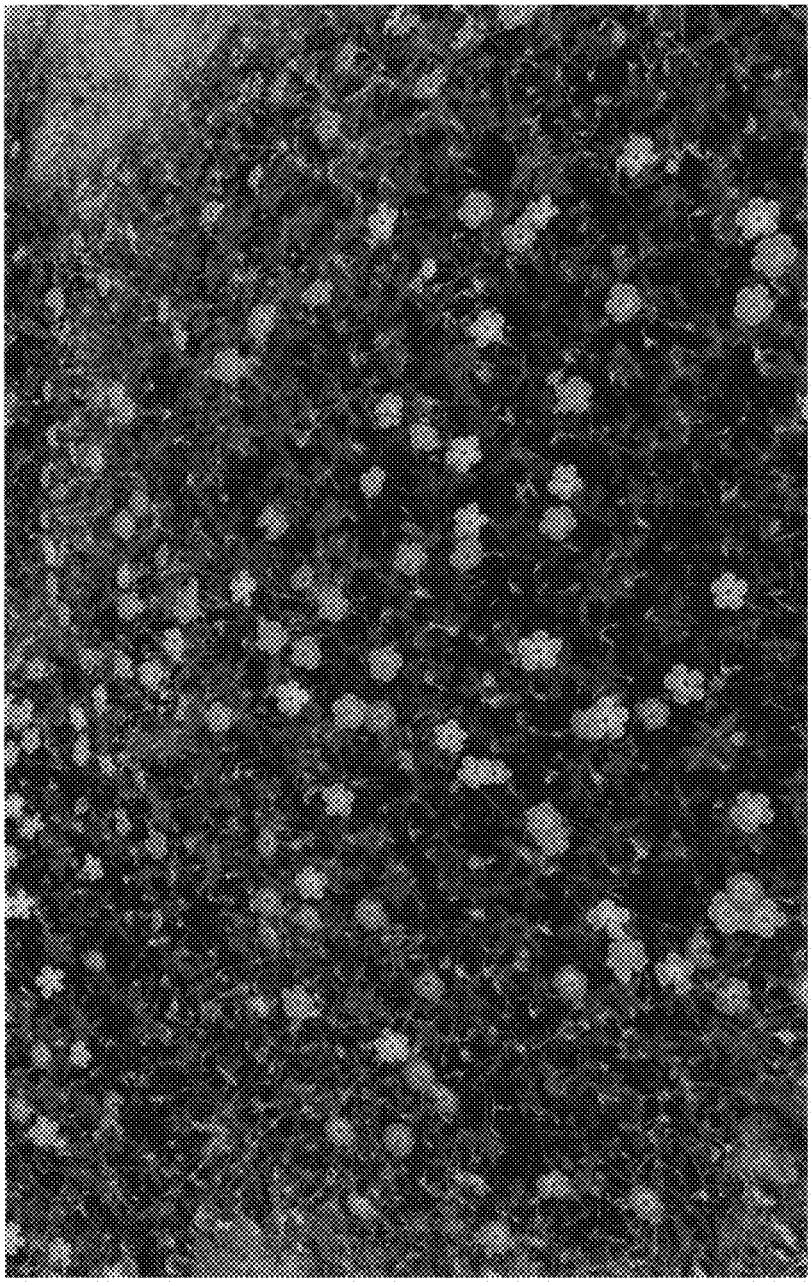
Figure 2:
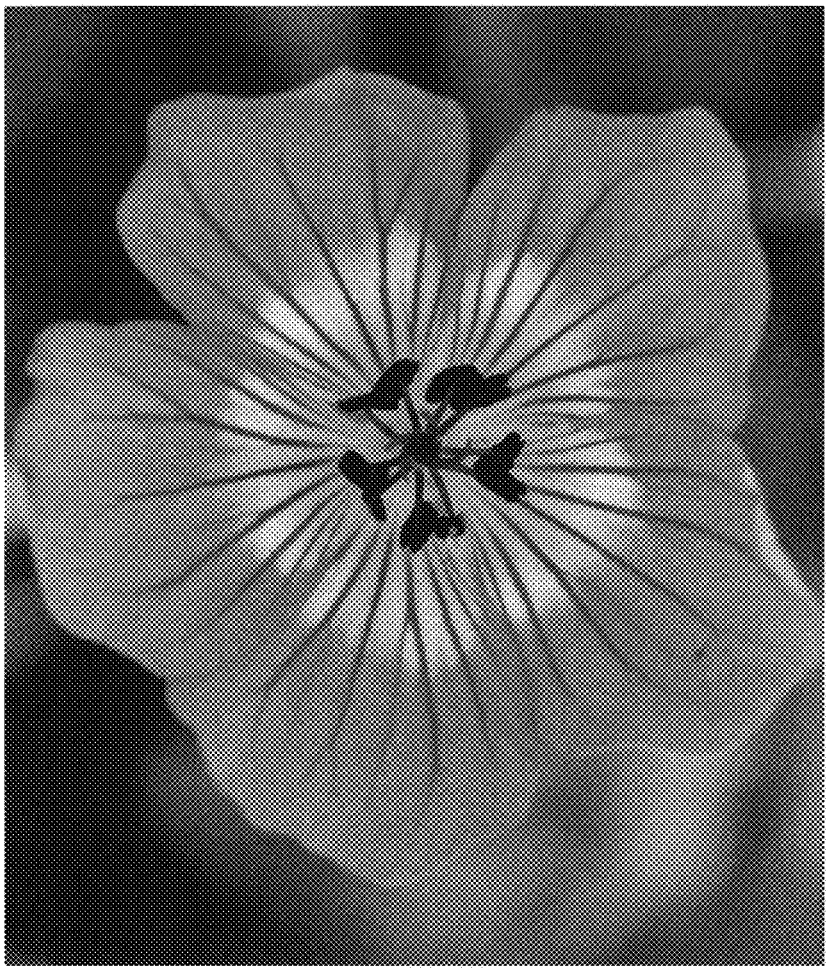
FIG. 2 illustrates in full color a close up of a flower of 'KELLY ANNE'.
Figure 3:
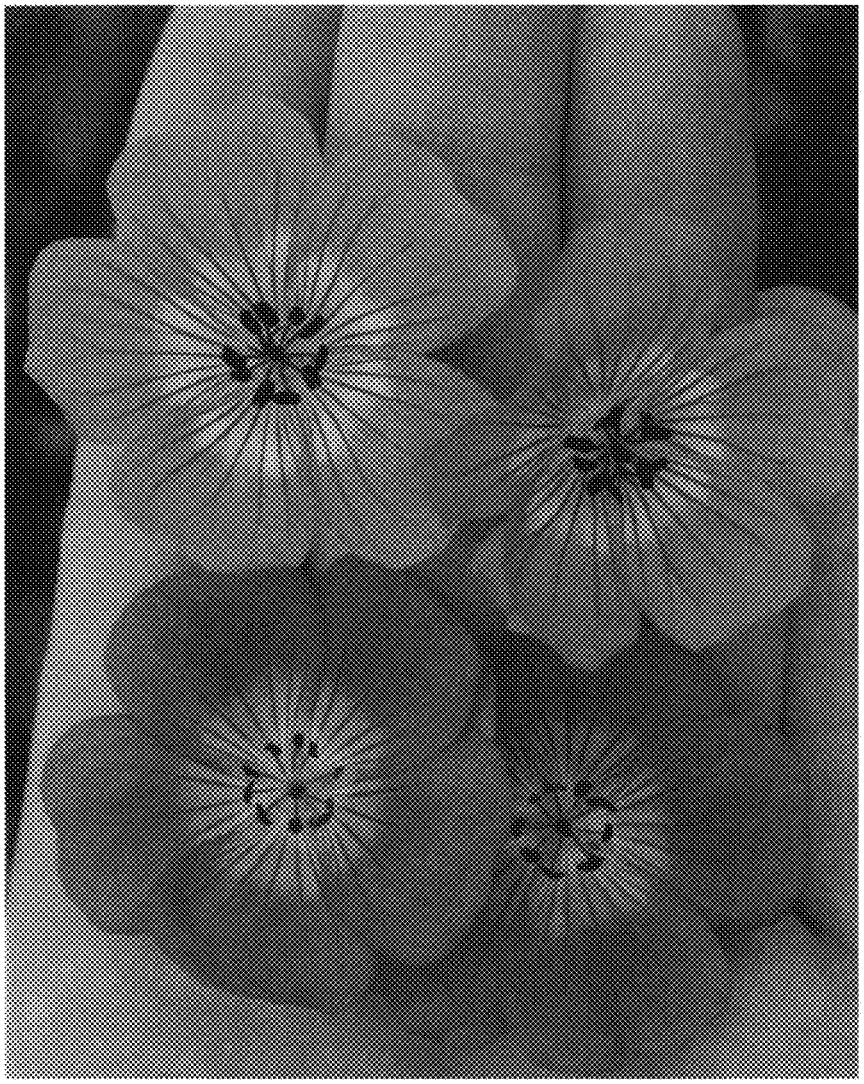
FIG. 3 illustrates a flower of the new variety on the right of the figure and a flower of the comparator 'Rozanne' on the left of the figure.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'KELLY ANNE' plants grown outdoors in Noordwijkerhout, the Netherlands. Temperatures ranged from −5° C. to 25° C. at night to 5° C. to 32° C. during the day. No artificial light, photoperiodic treatments were given to the plants. Measurements and numerical values represent averages of typical plant types.

Botanical classification: *Geranium wallichianum* 'KELLY ANNE'.

PROPAGATION

Typical method: Tissue culture.

PLANT

Growth habit: Upright and outwardly spreading flowering perennial.
Height: Approximately 45 cm.
Plant spread: Approximately 80 cm.
Pot size of plant described: Uncontainerized, plant in ground.
Age of plant described: Approximately 1 year.
Growth rate: Vigorous.

FOLIAGE

Leaf:
- *Arrangement*.—Alternate.
- *Average length* (*excluding petiole*).—Approximately 6.0 cm.
- *Average width*.—Approximately 8.0 cm.
- *Shape of blade*.—Palmate.
- *Depth of sinus*.—Medium.
- *Aspect*.—Flat to somewhat undulating and upwardly folded.
- *Apex*.—Acute.
- *Base*.—Sagittate.
- *Margin*.—Palmately cleft, lobes biserrate.
- *Depth of incisions on margin*.—Shallow.
- *Appearance*.—Matte.
- *Texture of top surface*.—Pubescent.
- *Texture of bottom surface*.—Pubescent.
- *Rugosity*.—Very weak.
- *Color*.—Young foliage upper side: Near Green 141B. Young foliage under side: Near Green 141B. Mature foliage upper side: Near Green 141B. Mature foliage under side: Near Green 141B.

Venation:
- *Type*.—Pinnate.
- *Venation coloration upper side*.—Near Yellow-Green 145A.
- *Venation coloration under side*.—Near Yellow-Green 145A.

Petiole:
- *Length*.—Average 7 cm.
- *Width*.—Approximately 0.2 cm.
- *Color*.—Near RHS Yellow-Green 145A, turning near Red 46B during in late Summer.
- *Strength*.—Very strong, flexible.
- *Texture*.—Pubescent.

Stipule: Not observed.

INFLORESCENCE

Natural flowering season: May until November in the Netherlands.
Quantity of flowers: About 200 flowers and flower buds per plant.
Flowers persistent or self cleaning: Petals not persistent, sepals persistent.
Fragrance: None detected.
Flower attitude: Upward and strongly outwards.
Flowering stem branching: Flowering occurs on both sides of the flowering stem.
Flower size:
- *Diameter*.—Approximately 4.0 cm.
- *Depth*.—Approximately 1.5 cm.

Petals:
- *Petal arrangement*.—5, in a single whorl. Unfused and very slightly overlapping.
- *Margin*.—Entire.
- *Apex*.—Obtuse to nearly truncate.
- *Length*.—Approximately 2.0 cm.
- *Width*.—Approximately 2.3 cm.
- *Shape*.—Deltoid.
- *Base*.—Attenuate.
- *Texture*.—Smooth, glabrous, all surfaces.
- *Aspect*.—Mainly flat, with upward cupping towards apex.
- *Color*.—When opening: Upper surface: Young Petals: Near Purple-Violet N80C with base near White N155D. Veins near Purple 77A. Mature Petals: Near Purple-Violet N80C with base near White N155D. Veins near Purple 77A. Lower surface: Young Petals: Near Purple-Violet N80C with base near White N155D. Veins near Purple 77A. Mature petals: Near Purple-Violet N80C with base near White N155D. Veins near Purple 77A.

Vein conspicuousness: Veins very strongly conspicuous, distributed throughout the flower.

Bud:
- *Shape*.—Ovate.
- *Length*.—Average 1.4 cm.
- *Diameter*.—Average 0. cm.
- *Color*.—Near Green 138B.

Sepals:
- *Quantity*.—5, in a single whorl.
- *Shape*.—Oblanceolate.
- *Length*.—Approximately 1.0 cm.
- *Width*.—Approximately 0.3 mm.
- *Margin*.—Entire.
- *Apex*.—Apiculate.
- *Base*.—Cuneate.
- *Texture*.—Smooth, glabrous. Margin pubescent.
- *Color* (*immature and mature*).—Upper surface: Near Green 137B. Lower surface: Near Green 138A.

Peduncles:
- *Length*.—Average range 1.5 to 3.6 cm.
- *Diameter*.—About 1.5 mm.
- *Color*.—Near RHS Yellow-Green 145A, flushed Red 46B from late Summer.
- *Aspect*.—Straight to somewhat undulating.
- *Texture*.—Pubescent.

Pedicels:
*Length*.—Average range 1.5 to 2.5 cm.
*Diameter*.—About 1 mm.
*Color*.—Near RHS Yellow-Green 145A.
*Aspect*.—Straight to somewhat undulating.
*Texture*.—Pubescent.
Floral bracts:
*Shape*.—Deltoid.
*Length*.—Average 8 mmm.
*Width*.—About 3 mm.
*Color*.—Near RHS Greyed-Red 181B.
*Texture*.—Papery.

REPRODUCTIVE ORGANS

Stamens:
*Number*.—Average 10.
*Filament length*.—Approximately 6 mm.
Anthers:
*Shape*.—Linear.
*Length*.—Approximately 3 mm.
*Color*.—Near RHS Purple 79A.
*Pollen*.—Not observed.
Pistil:
*Number*.—1.
*Length*.—Approximately 8 mm.
*Color*.—Near RHS Purple 79A.

OTHER CHARACTERISTICS

Disease resistance: Neither resistance nor susceptibility to the normal diseases and pests of *Geranium* has been observed.
Drought tolerance and cold tolerance: The new cultivar can tolerate cold temperatures to approximately −25° C. and tolerates an upper temperature range to at least 35° C.
Fruit/seed production: Not observed to date.

What is claimed is:
1. A new and distinct cultivar of *Geranium* plant named 'KELLY ANNE' as herein illustrated and described.

* * * * *